United States Patent [19]
Cribbs et al.

[11] 4,204,433
[45] May 27, 1980

[54] COMPUTERIZED ULTRASONIC SCANNER WITH TECHNIQUE-SELECT

[75] Inventors: Robert W. Cribbs, Placerville; John E. Mahony, Sacramento, both of Calif.

[73] Assignee: Litton Industrial Products, Inc., Beverly Hills, Calif.

[21] Appl. No.: 848,988

[22] Filed: Nov. 7, 1977

[51] Int. Cl.² ............................................. G01N 29/00
[52] U.S. Cl. ...................................... 73/620; 128/660
[58] Field of Search .................................. 73/618–626, 73/606, 607, 627, 629; 128/660; 340/5 MP; 358/112

[56] References Cited

U.S. PATENT DOCUMENTS

| | | | |
|---|---|---|---|
| 3,856,985 | 12/1974 | Yokoi et al. | 73/629 X |
| 4,058,001 | 11/1977 | Waxman | 73/620 |

OTHER PUBLICATIONS

R. J. Myrick et al, Real-Time Digital Echocardiography Using Burst Analog Sampling, IEEE Transactions on Sonics & Ultrasonics, Jan., 1977, pp. 19–23.

C. K. Chow et al, Digital Processor for Data Compaction & Image Enhancement of Echographical Signals, IBM Technical Disclosure Bulletin, vol. 17, No. 10, Mar. 1975, pp. 3154–3158.

*Primary Examiner*—Stephen A. Kreitman
*Attorney, Agent, or Firm*—Robert A. Seldon

[57] ABSTRACT

A computerized ultrasound scanner is disclosed having operator-actuable apparatus for selectively choosing one of a plurality of video processing techniques utilized to convert information from ultrasonic pulse reflections into a video displayed image of the interior region of an examined body.

6 Claims, 8 Drawing Figures

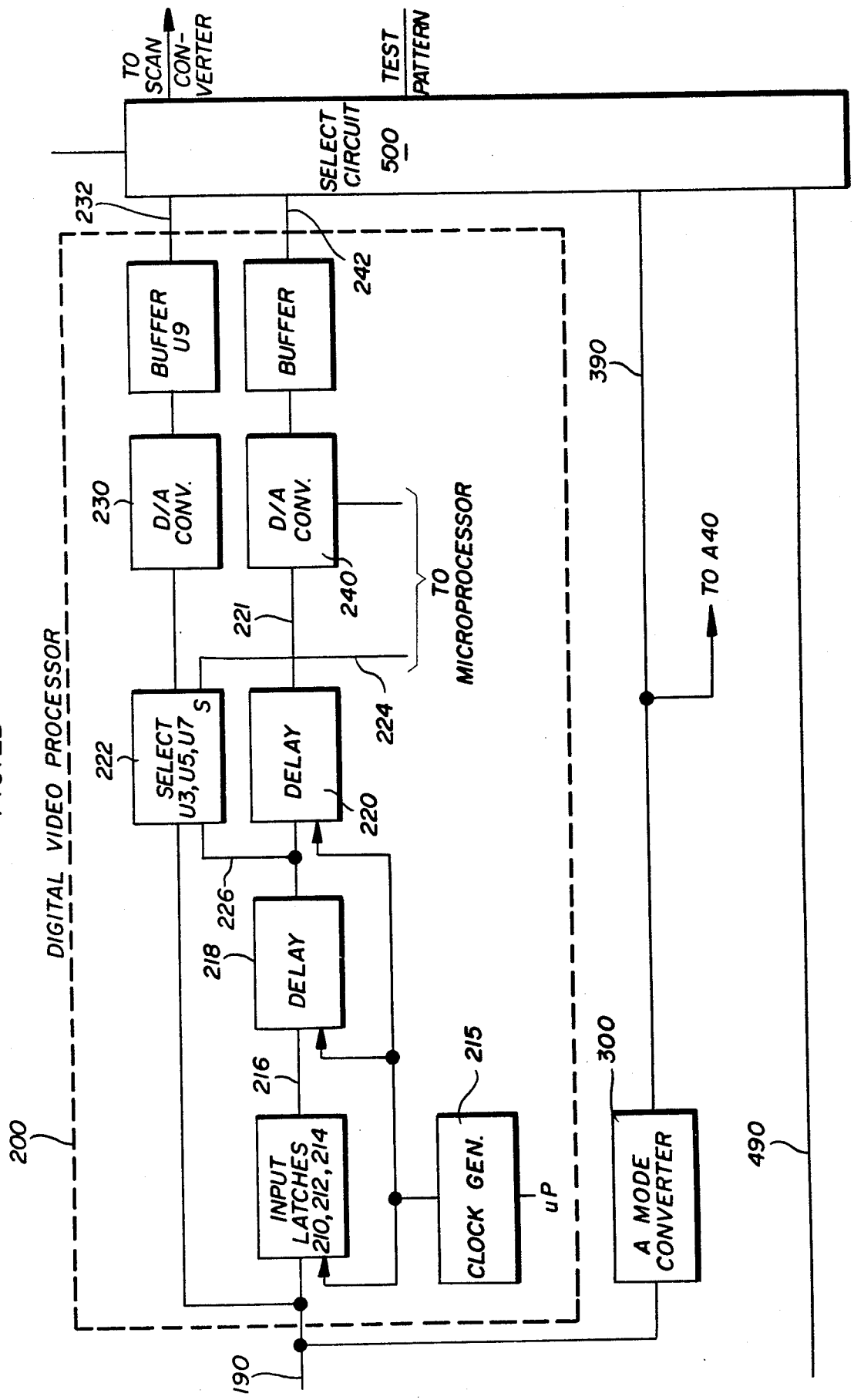

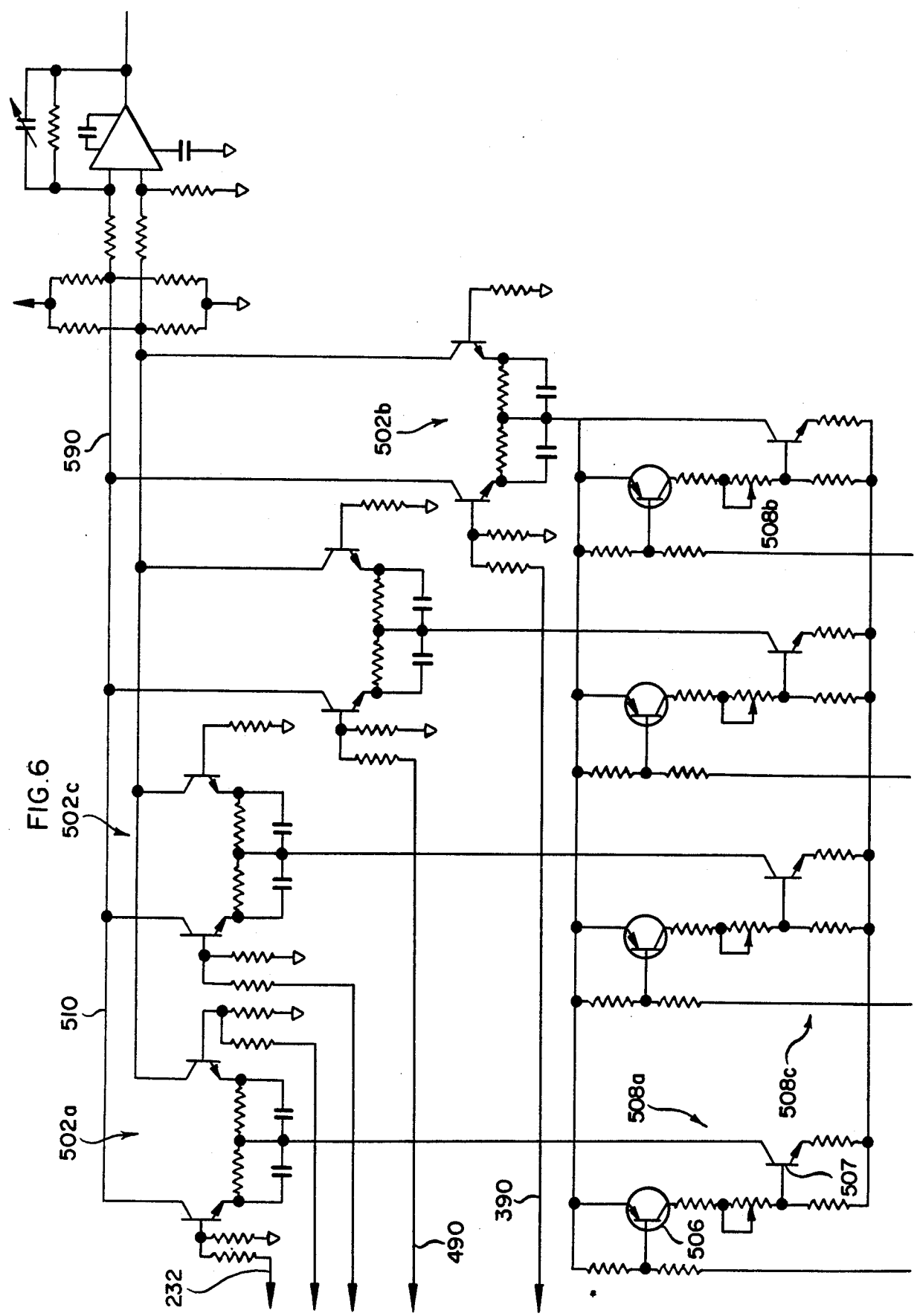

COMPUTERIZED ULTRASONIC SCANNER WITH TECHNIQUE-SELECT

FIELD OF THE INVENTION

1. Background of the Invention

This invention relates to ultrasonic systems particularly suited for medical diagonstic techniques. As is known in the art, ultrasonic systems may be generally described as comprising means for generating a series of ultrasonic pulses into a patient's body, means for detecting reflected pulses, means for deriving and processing information related to the return time and amplitude of each reflection, and means for displaying video image in accordance with the processed information. These systems are capable of displaying images of internal organs of a body which are generally similar in appearance to images derived by x-ray techniques. With the increasing alarm concerning the cumulative effects of exposure to x-rays, ultrasonic techniques have acquired importance as a safe alternative.

The acceptance and use of ultrasonic techniques will largely depend upon the quality of image definition; that is to say, the clarity and accuracy of the imaged information. Image definition is dependent upon the manner by which the reflection signal is processed prior to display. Accordingly, this invention relates, more particularly to the signal processing of the reflection information prior to its display.

2. Summary of the Prior Art

Many signal processing techniques are known in the art and are selectively used in accordance with the particular body organ under observation, the operating mode of the ultrasonic system, and the type of diagnosis being performed. For example, the location of the edge of an organ, rather than its structure, may be of concern in the M-mode where the motion of a heart valve is to be observed, or in the B-mode where the enlargement of an organ, such as a kidney, is of concern. The B-mode signal-processing technique used will necessarily differ, however, when the structural detail of an organ is the subject of interest. Further, the technique will differ if the organ is the liver, where fine structure is to be viewed, or a fetus where a low dynamic range is needed to eliminate echos generated by the placenta. Additionally, there is a subjective factor whereby different individuals prefer the results of different process techniques.

SUMMARY OF THE INVENTION

It is accordingly an object of the present invention to provide in an ultrasonic system of the type including ultrasonic pulse generating means for applying a series of pulses to the surface of a body for propagation therethrough, detecting means responsive to the emergence of reflected pulses from the body for producing a respective incoming signal indicative of a discontinuity in the propagation path, and video display means responsive to the incoming signals for producing a visual representation of the media defining the propagation path. The system disclosed herein additionally comprises operator-actuable means for producing a control signal related to a selected one of a plurality of signal processing techniques which condition the incoming signal for video displaying memory means for storing information related to the signal processing techniques, memory access means responsive to the unique control signal for obtaining the stored information related to the selected technique, and means receiving the incoming signal and responsive to the access means in accordance with the accessed information for selectively producing an appropriately processed video signal.

These and other features of the invention will be readily apparent from the detailed description set forth below in conjunction with the following drawings.

BRIEF DESCRIPTION OF THE DRAWING

FIG. 2 is a perspective view of a control console of the presently described system which provides a plurality of operator-selectable video processing techniques.

FIGS. 2A and 2B, together form a block diagram of the preferred video processing system constructed in accordance with the invention.

FIG. 6 is a schematic diagram of the technique-selecting circuit of FIG. 2.

For the sake of clarity, corresponding components and signals throughout the Figures have been identically referenced.

DESCRIPTION OF THE PREFERRED EMBODIMENT

Figure 1:
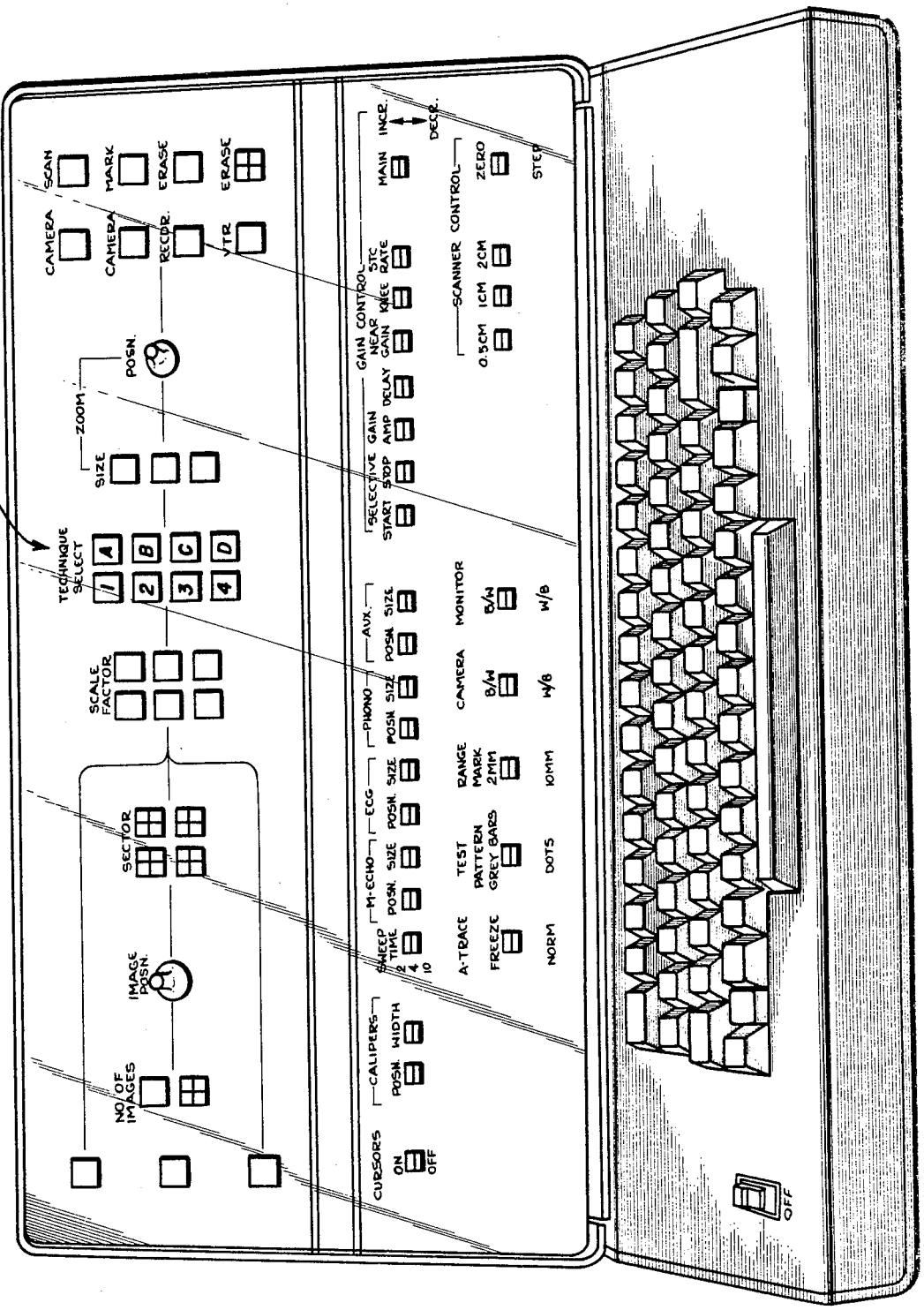

FIG. 1 is a perspective view of a control console for use in the ultrasonic system of the present invention. For the sake of brevity, the functions of the console 10 which are not germane to the presently described invention are not described. Attention should however, be directed to a two column by four row matrix of push-buttons 12 which provide operator-selectable means by which the desired video processing technique is chosen. The columns of buttons are numerically and alphabetically labelled 1–4 and A–D respectively, and it is, of course, obvious that fewer or more buttons may be provided.

For the sake of discussion, it will be assumed that the matrix provides a choice of the following video-processing techniques:

1. Analog process
2. Digital contour process
3. Analog bistable process
4. Digital edge-enhancement process Wherein:

A. provides greater dynamic range
B. provides small dynamic range
C. provides moderate edge-enhancement
D. provides greater edge-enhancement With respect to technique number 4, it is additionally possible to have, for example, 4AD which provides increased dynamic range with a large degree of edge enhancement. For each technique selected, a unique control signal or combination of control signals, is produced which, applied to a microprocessor, controls the manner by which the information content of the incoming ultrasonic reflections is processed.

Figure 2A:
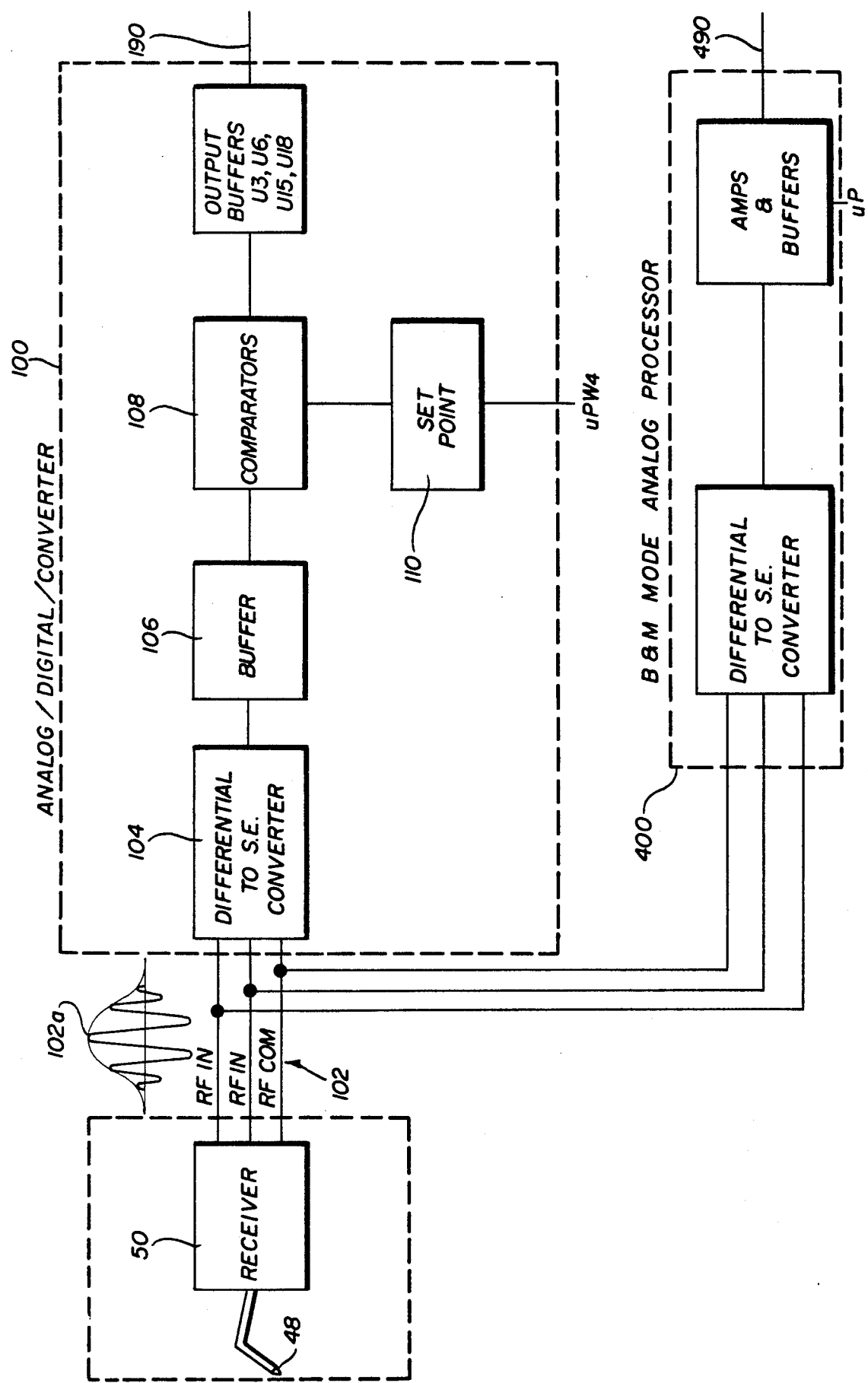

FIG. 2A and 2B, together, form a block diagram of a video processing system in accordance with the invention. As will be shown hereinbelow, the microprocessor of the presently disclosed system is responsive to the control signal produced at the console to access a memory associated with the microprocessor and send appropriate instructions and information stored therein to the system hardware. The video processing system is shown to comprise an analog-to-digital converter 100 coupled to a pulse receiver 50 to receive an incoming electrical signal 102 therefrom. The analog/digital converter 100 is coupled at its output to a digital video processor 200 and to an A-mode converter 300. Also coupled to the receiver 50 is a B/M mode analog processor 400. The processors 200, 400 and converter 300 are coupled to the input side of a process-selecting circuit 500 which places the appropriate processed video signal at the input of a scan conversion memory for storage and display of the processed information in accordance with any of a variety of methods known in the art.

The signal 102 is produced by the receiver 50 in response to ultrasonic reflections, emerging from a body being examined, and detected by a transducer 48. The incoming signal 102 defines a generally pulse shaped envelope 102a, the amplitude characteristics which are indicative of the acoustical impedance change at the reflection-generating discontinuity in the path of the transmitted pulse.

The incoming signal 102 is first quantized by level and converted to a digital form. The quantizing levels are determined by pre-programmed values which can be changed as a function of the technique selected. As will be more clearly explained, the output signal from the digital/analog converter 100 comprises a plurality of lines, each having a binary value indicative of whether the incoming signal 102 is higher or lower than the value of that line, as determined by the pre-programmed value associated therewith.

Figure 3:
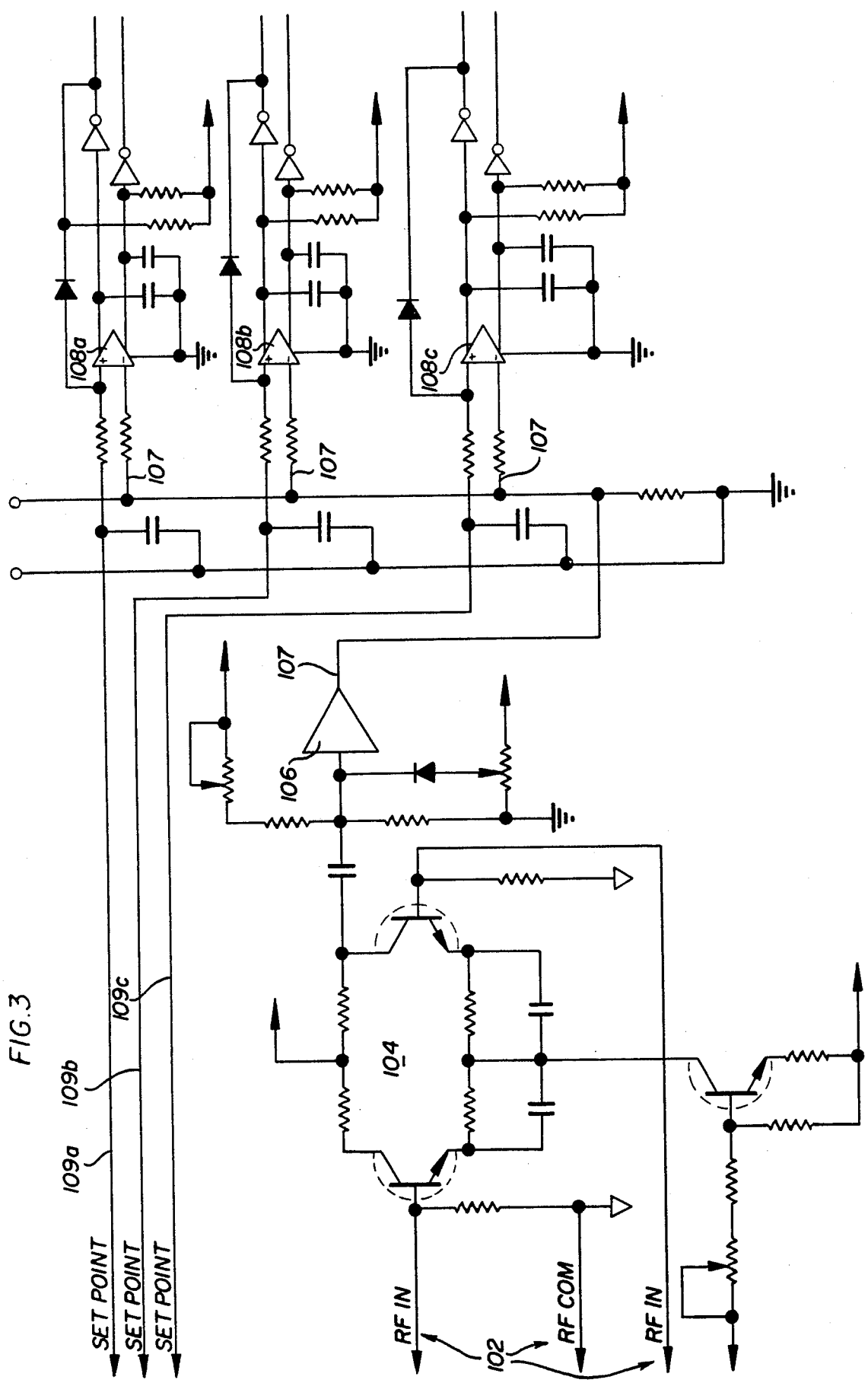
FIG. 3 is a schematic diagram of a preferred configuration for the analog-to-digital converter of FIG. 2A.

Referring to FIG. 3 in conjunction with FIG. 2A, it may be appreciated that the incoming signal 102 is differentially fed by the receiver 50 to a differential-to-single-end converter 104. The converter output 107 passes through a buffer 106 to the inverting input terminal of a plurality of comparators illustratively shown as 108 a–c. The comparators track the level of the single ended converter 107 and determine when it is greater than a respective set point. Applied to each of the non-inverting inputs of the comparators 108 a–c is a respective voltage level 109 a–c which provides the comparator set point. The values of the plurality of applied voltage levels are pre-programmed into memory at addresses associated with the selected technique, and are part of a greater plurality which represent all techniques available to the operator for selection.

Since the output of each comparator 108 A, B, C, is either a "1" or "2", depending on whether the incoming signal is greater than or less than the respective set point, the output from the converter 100 comprises a plurality of binary numbers which, together, form a binary word quantizing the instantaneous magnitude of signal 102. In the disclosed embodiment, the comparator outputs assume a "LO" or "0" binary state when the respective set point value is exceeded. In practice, twelve such comparators have been found to provide optimum results.

Figure 4:
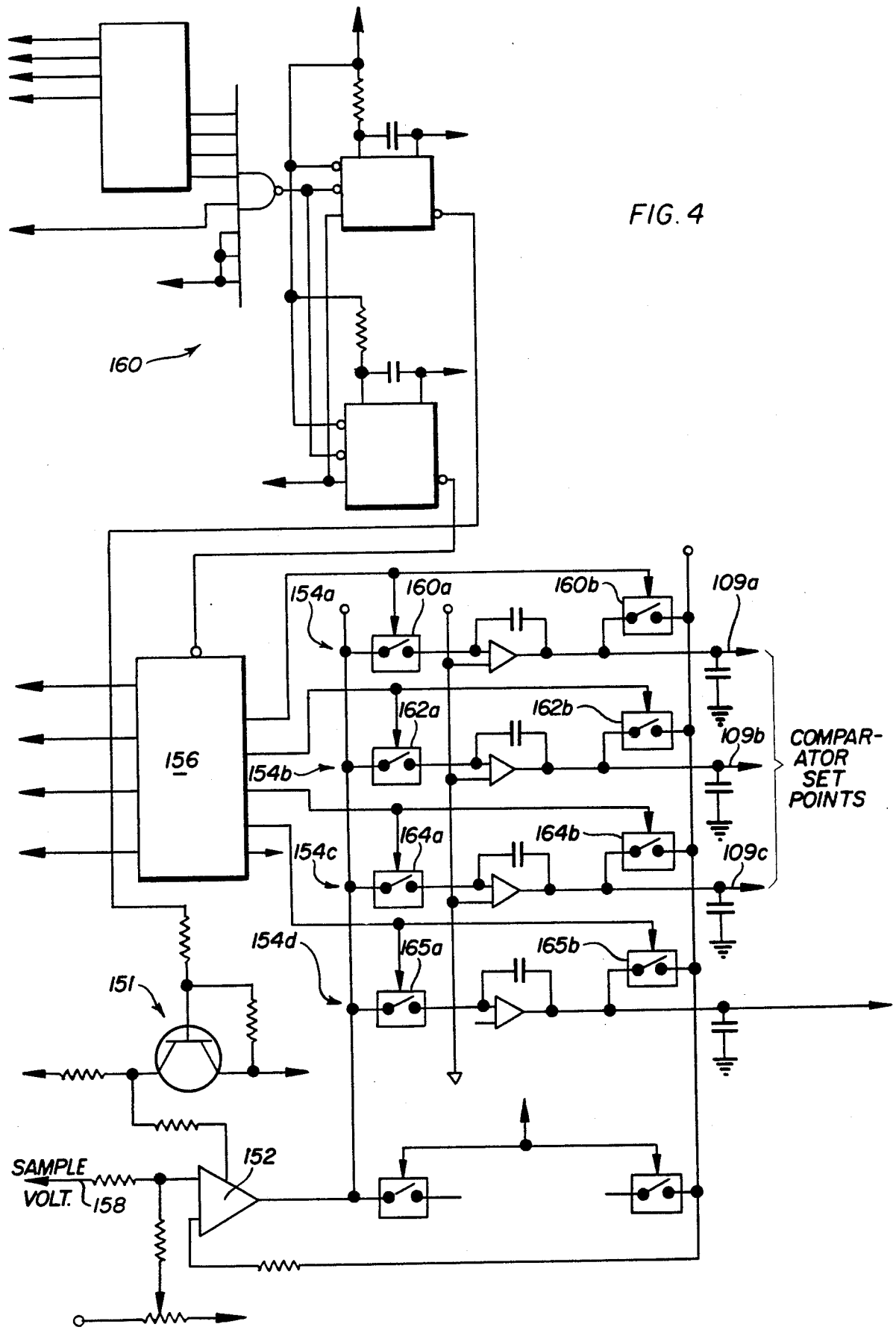
FIG. 4 is a schematic diagram of a preferred sample-and-hold circuit arrangement for use with the converter of FIG. 3

Examining in detail the manner by which the set point voltage levels are applied to the comparators 108 a, b, c, reference should be made to FIG. 4 which depicts, in schematic form, a preferred sample-and-hold circuit in a demultiplexed style system wherein an amplifier 152 drives a plurality of sample and hold devices illustratively shown as 154 a,b,c,d. In practice, the number of sample and hold devices 154 correspond to the number of comparators 108 (FIG. 3). An analog sample voltage 158 is momentarily applied to an input amplifier 152 which is gated on via switch means 151 in response to gate signals from a timing circuit 160. Gate signals from the timing circuit also control the timing of the opening and closing of individual sample and hold switches 160 a,b, 162 a,b and 164 a,b. The appropriate switches are opened and closed by the demultiplexer 156, which is responsive to an address placed at its input.

In operation, the microprocessor accesses the appropriate set point values from memory, in accordance with the selected video processing technique and momentarily places corresponding analog voltages on the "sample voltage" line 158 while addressing the appropriate sample and hold devices 154 a–d through the demultiplexer 156. The input amplifier 152 is gated "on" to update the addressed sample and hold circuit in accordance with input signal 158. After a period of time, the timing circuit 160 shuts the amplifier 152 off, but leaves the demultiplexer 156 on to minimize "glitches" generated by the opening and closing of the sample and hold circuit. Further details concerning the operation of this circuit may be found in a co-pending U.S. application Ser. No. 848,989, entitled "Sample and Hold Circuit" filed concurrently herewith by John Mahony, assigned to the present assignee, and hereby incorporated by reference.

Returning to FIG. 2A and 2B, the output signal 190 from the digital-to-analog converter 100 has been shown, above, to be a multi-bit digital number representing the instantaneous magnitude of the incoming signal 102. It may be appreciated that the effect of the set point setting circuit 110 is to vary the transfer function of the converter 100 and, therefore, the dynamic range of the system in accordance with the preprogrammed values, in memory, which are associated with each signal-processing techniques available for selection. The output 190 is simultaneously applied to a digital video processor 200, and an A-mode converter 300. The A-mode carrier is preferably configured in the manner taught by our co-pending U.S. Patent Application, U.S. Ser. No. 848,987, now U.S. Pat. No. 4,172,386, filed concurrently herewith, and entitled, "Video-Formatted A-Trace Converter for Ultrasonic Diagnostic Systems", the content of which is hereby incorporated by reference. For the purposes of this discussion, the A-mode converter 300 may be viewed as a device which converts the unprocessed digital video signal 190 into a signal which is compatible with the video monitor and from which an A-trace may be accordingly displayed in responses to the selection of the A-mode by the operator.

Figure 5A:
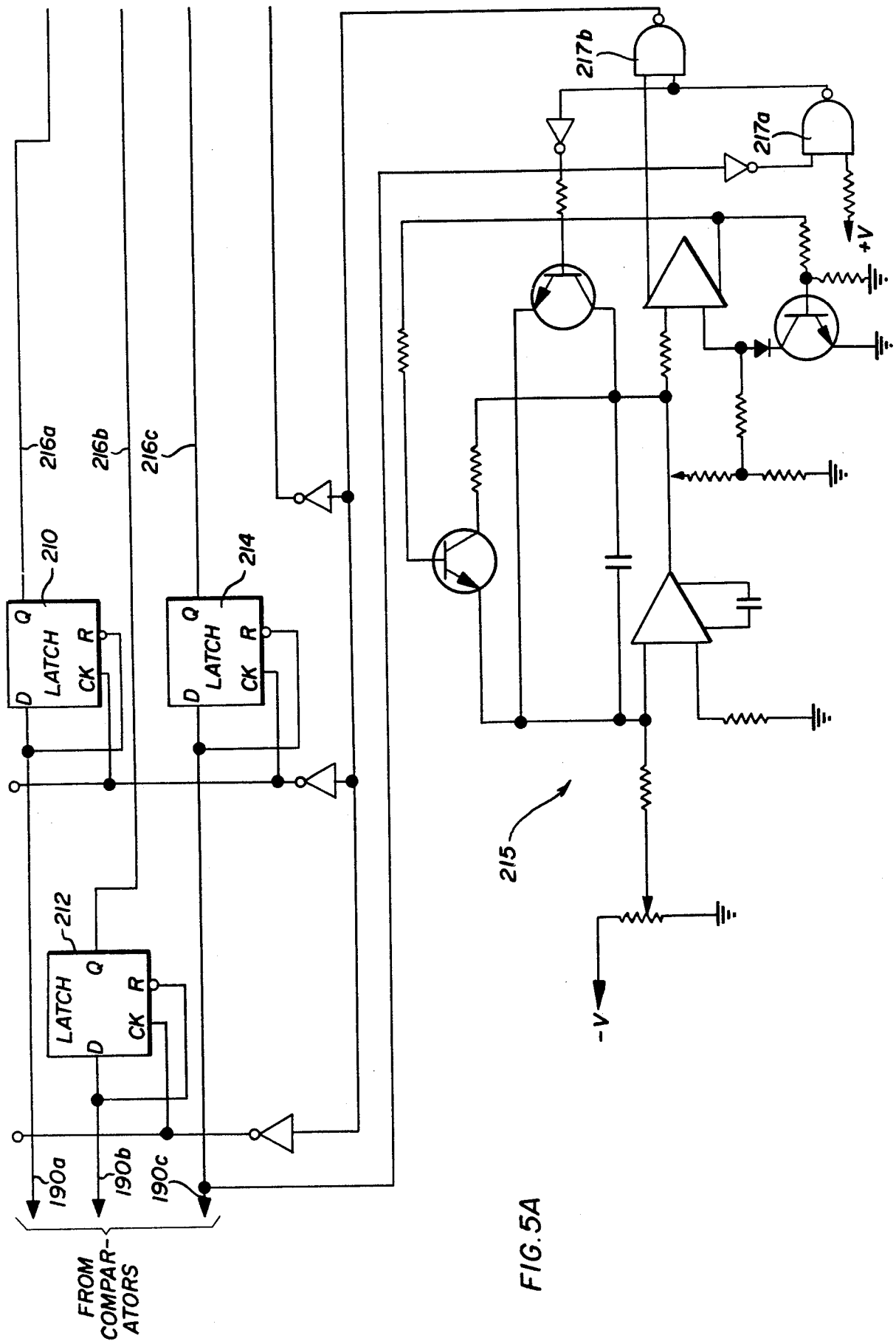
FIGS. 5A and 5B together form a schematic diagram of the digital video processor of FIG. 2B.
Figure 5B:
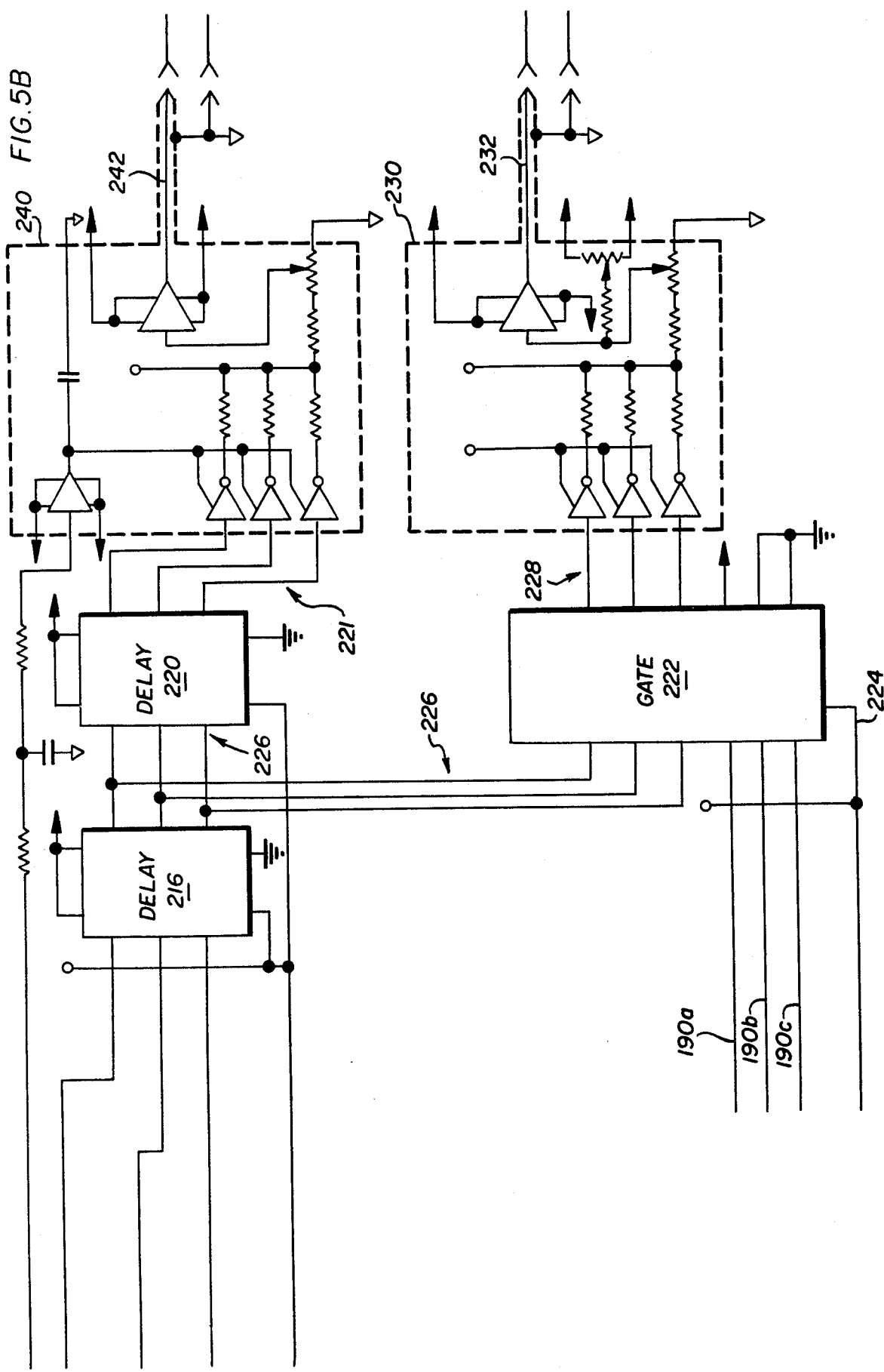

While an overview of the digital video processor 200 is more clearly appreciated with reference to FIG. 2B, a more detailed understanding may be had by reference to FIGS. 5A and 5B. It is first desirable to detect the peak signal value of each reflection. Naturally, the peak may occur at any time during receipt of the envelope 102a so that the sampling and holding of the incoming signal 102 at a particular discrete time, only would likely miss the peak value. Basically a plurality of latches 210, 212, 214 are therefore provided, to produce an output signal which follows an increasing incoming signal 190, but which only clocks down as the incoming signal 190 decreases. The maximum value is thereby "frozen" for acceptance by remaining circuitry, and, additionally, the latches 210, 212, 214 substantially hold each pre-maximum peak within the envelope until a larger peak is sampled. The latches are then cleared before the next reflection. As shown in FIG. 5A, the comparator output signals 190 *a,b,c,* from the converter 100 are first passed into respective latch circuits 210, 212, 214, which, as explained, latch the maximum value attained by the signals 190 *a,b,c,* respectively, until released. The latches are clocked by a clock generator 215 which is gated by means 217 *a,b,* when the comparator having the lowest set point is tripped; i.e. comparator 180*c* in the illustrated embodiment. Each latch 210, 212, 214 thereafter samples the associated comparator signal 190 *a–c* at the rising edge of each clock pulse and, because the reset terminal R is coupled to the input terminal D, is reset when the associated comparator is tripped by the passing of its respective set point by the incoming signal 102 (FIG. 1). The reset latches 210, 212, 214 remain in their reset state until the incoming signal has decreased below the set point of the associated comparator. The now-activated latches are then clocked to reproduced on output lines 216*a–c* the instantaneous signal level on the lines 190 *a–c.* Thus, the latches 210, 212, 214 co-operate to "freeze" the peak value of the incoming signal 102 (FIG. 1) until the next succeeding circuitry is ready to accept it.

The outputs 216 *a–c* from the latches 210, 212, 214, are passed through one stage of delay 218 and applied in parallel to a second stage of delay 220, emerging as a twice-delayed signal 221, and to a gate circuit 222. Also applied to the gate circuit 222 are the comparator 108 *a–c* output signals so that the selector circuit 222 may choose the undelayed signals 190 *a–c* when a control signal 224 from the microprocessor indicates that the contour processing has been selected; alternately, the selector circuit passes the once delayed signals 226 if the signal 224 indicates that the image is to be edge-enhanced. In either case, the selected signals 228 are applied to a digital-to-analog converter 230, which produces a video signal 232. In both the contour and edge-enhancement modes the video signal 242 from the converter 240 represents the twice-delayed signal 221. The two video signals 232, 242 are respectively applied as inputs to a technique-select circuit 500, shown in FIG. 2B.

Also applied to the circuit 500 are the output signals from the A-trace converter 300 and the "B/M" Analog Processor" 400. Turning to the process selector circuit 500, which applies appropriately processed information from the ultrasonic reflection to the scan converter for storage and display, attention should be directed to FIG. 6. Generally, the various video signals 212, 242, 390, 490 (FIG. 5B) are applied as input signals and, by means now described selectively gated into a common output buss 590 in accordance with the operator-selected mode and technique.

Accordingly, the video signal 232, 242 from the digital video processor 200 (FIG. 5B) are applied to opposite inputs of a differential amplifier 502*a*. The remaining signals 390, 490, are applied to respective inputs of respective differential amplifiers 502 b,c, the opposing inputs of the latter being coupled to common.

The amplifiers 502 *a,b,c* are selectively activated in accordance with the selected technique by means of respective selectively-energized sources 508 *a–c* of generally constant current so that the appropriate video signal is placed on the output buss 590. To energize the proper amplifier, the system microprocessor addresses a plurality of control lines 504 *a–c* in accordance with information accessed from memory in response to the selected technique and mode. Assuming that the digital technique was selected, control line 504*a* will go "LO", while the lines 504 *b,c* remain "HIGH". Transistor 506 is on and amplifier 507 is on, thereby activating differential amplifier 502*a*. The output signal 510 from the amplifier 502*a* is the difference between video signals 232 and 242. Since the signal 242 is the twice-delayed video signal of selected amplitude, the signal 590 is accordingly the edge-enhanced signal.

While the foregoing description describes a preferred embodiment of the invention, it should be understood that many variations and modifications which are obvious to those skilled on the art are included within its scope. The invention is therefore to be defined only by the claims appended thereto.

We claim:

1. In an ultrasonic diagnostic system of the type including ultrasonic pulse generating means for applying a series of pulses to the surface of a body for propagation therethrough, detecting means for detecting pulse reflections and responsive to the emergence of reflected pulses from the body for producing a respective incoming signal indicative of a discontinuity in the propagation path, and video display means for producing a visual representation of the media defining the propagation path, the improvement comprising:

operator-actuable means for producing a control signal related to a selected one of a plurality of signal processing techniques which condition the incoming signal for video displaying;

memory means for storing information related to the signal processing techniques;

memory access means responsive to the unique control signal for obtaining the stored information related to the selected technique;

circuit means for quantizing the amplitude of the incoming signal in accordance with the information accessed by the access means and for producing a first signal indicative thereof;

means receiving the first signal and responsive to the access means in accordance with the accessed information for selectively producing as a processed video signal either the first signal or a signal representing the subtracting of time-delayed portion of the first signal level from the instantaneaous level of the data signal to produce.

2. The system of claim 1 wherein the incoming signal has a multi-peaked waveform defined by generally pulse shaped envelope and the quantizing means includes analog-to-digital conversion means coupled to the detecting means for producing a digital output signal representative of the incoming signal magnitude and including means conditioned by the access means for varying the dynamic gain of the conversion means in accordance with the selected technique.

3. The system of claim 2 wherein the conversion means includes comparator means coupled to the detecting means to receive the incoming signal and arranged to compare the incoming signal to each of a plurality of threshhold levels for producing a binary output signal indicative of whether the received incoming signal level is higher than or lower than each threshold level; and means momentarily coupled to the access means for applying the appropriate threshold levels to the comparators in accordance with the binary information associated with the selected technique.

4. The system of claim 3 wherein the threshold level means includes sample and hold circuit means.

5. The system of claim 1 wherein the quantizing means includes a plurality of comparator circuits arranged to receive the incoming signal in an essentially simultaneous manner and to compare the incoming signal value with a respective one of a plurality of threshold levels, a plurality of sample and hold circuits arranged to apply a respective threshold level to each comparator circuit and to be timely coupled to the access means for sampling a level-indicative signal therefrom.

6. The system of claim 5 including operator-actuatable means for selectively varying the threshold level by the sample and hold circuits.

* * * * *

UNITED STATES PATENT AND TRADEMARK OFFICE
CERTIFICATE OF CORRECTION

PATENT NO. : 4,204,433
DATED : May 27, 1980
INVENTOR(S) : Cribbs, et al.

It is certified that error appears in the above-identified patent and that said Letters Patent are hereby corrected as shown below:

Column 6, Line 51: delete "to produce"

Signed and Sealed this

Fourteenth Day of July 1981

[SEAL]

Attest:

Attesting Officer

GERALD J. MOSSINGHOFF

*Commissioner of Patents and Trademarks*